(12) United States Patent
Bardapurkar et al.

(10) Patent No.: US 10,222,308 B2
(45) Date of Patent: Mar. 5, 2019

(54) TIME/AMPLITUDE DOMAIN REFLECTOMETRY AS A TECHNIQUE FOR MEASUREMENT OF SURFACE WETTABILITY

(71) Applicant: HALLIBURTON ENERGY SERVICES, INC., Houston, TX (US)

(72) Inventors: Sameer Bardapurkar, Pune (IN); Venkata Gopala Rao Palla, Pune (IN); Abhimanyu Pramod Deshpande, Pune (IN)

(73) Assignee: Halliburton Energy Services, Inc., Houston, TX (US)

( * ) Notice: Subject to any disclaimer, the term of this patent is extended or adjusted under 35 U.S.C. 154(b) by 120 days.

(21) Appl. No.: 15/516,660

(22) PCT Filed: Nov. 13, 2014

(86) PCT No.: PCT/US2014/065413
§ 371 (c)(1),
(2) Date: Apr. 3, 2017

(87) PCT Pub. No.: WO2016/076870
PCT Pub. Date: May 19, 2016

(65) Prior Publication Data
US 2017/0292902 A1 Oct. 12, 2017

(51) Int. Cl.
*G01N 13/00* (2006.01)
*E21B 47/01* (2012.01)
(Continued)

(52) U.S. Cl.
CPC ............ *G01N 13/00* (2013.01); *E21B 47/01* (2013.01); *E21B 49/003* (2013.01); *G01N 27/221* (2013.01)

(58) Field of Classification Search
CPC .......... E21B 47/00; E21B 47/01; E21B 49/00; E21B 49/003; G01N 13/00; G01N 27/22
(Continued)

(56) References Cited

U.S. PATENT DOCUMENTS 3,981,181 A * 9/1976 Ochiai .................. G01M 3/045
73/40.5 R
H1932 H * 1/2001 Heathman et al. ...... 166/250.14
(Continued)

OTHER PUBLICATIONS

PCT International Search Report and Written Opinion, dated Aug. 13, 2015, Appl No. PCT/US2014/065413, "Time/Amplitude Domain Reflectometry as a Technique for Measurement of Surface Wettability," Filed Nov. 13, 2014, 13 pgs.

*Primary Examiner* — Benjamin R Schmitt
(74) *Attorney, Agent, or Firm* — John Wustenberg; Parker Justiss, P.C.

(57) ABSTRACT

A surface wettability measurement method for determining the surface wettability of a surface for operations that require the removal of oil-based fluid such as cementing operations in an oil/gas environment. Time domain reflectometry (TDR) measurements are used to measure the wettability in a wellbore downhole during operations or in a lab environment when fluid flow is present. A surface wettability measurement system for determining the surface wettability of a surface located either in a wellbore downhole or in a laboratory setting using time domain reflectometry for measurements during operations when fluid flow is present.

18 Claims, 7 Drawing Sheets

(51) Int. Cl.
 *E21B 49/00* (2006.01)
 *G01N 27/22* (2006.01)
(58) Field of Classification Search
 USPC ...... 73/104, 152.01, 152.18, 152.19, 152.43, 73/866
 See application file for complete search history.

(56) References Cited

U.S. PATENT DOCUMENTS

| | | |
|---|---|---|
| 6,441,622 B1 | 8/2002 | Wrzesinski et al. |
| 8,766,641 B2 | 7/2014 | Pindiprolu et al. |
| 2008/0211521 A1 | 9/2008 | Lock |
| 2010/0289502 A1 | 11/2010 | Woodhead et al. |
| 2013/0033272 A1 | 2/2013 | Folgeroe et al. |
| 2013/0214803 A1 | 8/2013 | McFarlane et al. |
| 2014/0060819 A1 | 3/2014 | Pindiprolu |

\* cited by examiner

TIME/AMPLITUDE DOMAIN REFLECTOMETRY AS A TECHNIQUE FOR MEASUREMENT OF SURFACE WETTABILITY

BACKGROUND

This invention is related to the oil and gas industry. Preparing the wellbore and casing surface before placing cement in the annulus is an important step in achieving successful cement bonding between the casing surface, the borehole, and the cement. While drilling operations use drilling fluids (known as mud) to balance formation pressure and carry away drilling debris, cementing operations use a water-based cement that does not adhere well to surfaces coated with oil. To achieve proper bonding between cement and the casing surface, the casing surface should therefore be cleaned of oil-based fluids in order for the water-based cement to adhere properly. To displace and clean the surfaces of oil-based fluids, water-based fluids are pumped through and around a casing and borehole. However, there is a need for determining when the casing surface is clean (also known as being "water-wet").

One non-invasive technique to determine surface wettability of a surface is by using Electrochemical Impedance Spectroscopy (EIS), which has the potential to be performed at high pressure/high temperature (HPHT) conditions, and which is referred to in U.S. Pat. No. 8,766,641 and US application 2014/0060819. However, the EIS techniques described requires that the system to be in a static condition while the EIS data is being logged. This is a major drawback for using EIS as normal operations need to be halted. Furthermore, both in the field and in the laboratory, the mathematical modeling effort involved in employing EIS may restrict its use by someone who is not an expert in that area of expertise. In addition, the data logging equipment used in EIS is expensive.

BRIEF DESCRIPTION OF THE DRAWINGS

Accordingly, there are disclosed in the drawings and the following description methods and systems for measuring the surface wettability of a surface using time domain reflectometry (TDR).

Figure 1:
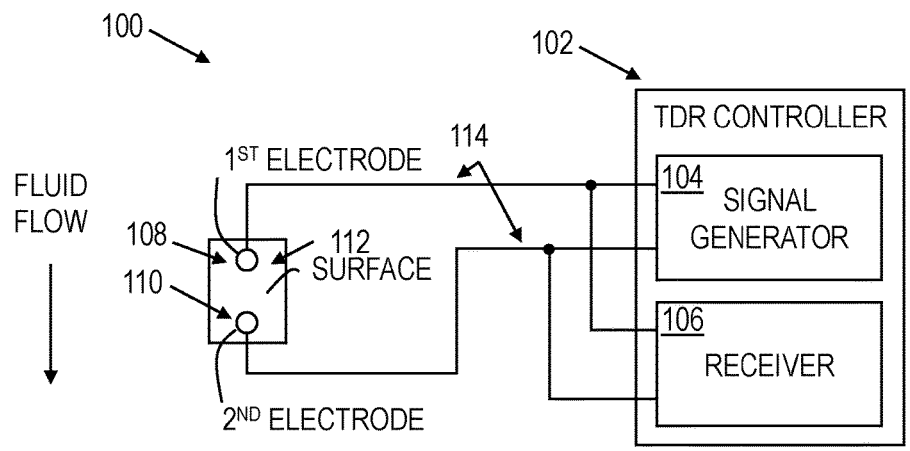
FIG. 1 is a block diagram of a surface wettability test apparatus.

It should be understood, however, that the specific embodiments given in the drawings and detailed description thereto do not limit the disclosure. On the contrary, they provide the foundation for one of ordinary skill to discern the alternative forms, equivalents, and modifications that are encompassed together with one or more of the given embodiments in the scope of the appended claims.

DETAILED DESCRIPTION

Disclosed herein are methods and systems to measure surface wettability (wettability) of a surface employing time domain reflectometry (TDR), where wettability is defined as "the ability of a solid surface to reduce the surface tension of a liquid in contact with it such that it spreads over the surface and wets it". For example, a casing coated with oil-based drilling fluid undergoes a cleaning step using water-based spacer fluid. The progress of the cleaning can be monitored using a series of TDR measurements at the casing during cleaning. Using the results of the measurements, the operator can decide on several courses of action including continuing cleaning, changing the fluid properties, or terminating the cleaning process.

TDR is a measurement technique used to determine the characteristics of dielectric media by observing reflected waveforms. For example, the impedance of a discontinuity along an electrical or optical transmission line can be determined from the amplitude and polarity of the reflected signal. When the amplitude of the reflected pulse is studied, then this technique is known as "Amplitude Domain Reflectometry". When the frequencies of the incident and reflected pulses are studied, then this technique is known as "Frequency Domain Reflectometry". However, it must be noted that, though there might be a plurality of such techniques, the underlying principle remains the same. The location of the reflecting impedance can also be determined from the time that a pulse takes to travel to and from the discontinuity. One advantage of using TDR measurements to determine surface wettability of a surface is that readings can take place in a dynamic environment such as during fluid flow (as compared to EIS which requires static conditions in order to work). One characteristic of fluid flow in a region around a casing downhole is the presence of shear force which is exerted on the surface of the casing. When a water-based fluid is in motion and a shear force is generated, this shear force acts to displace the existing oil film on an oil-wet surface and "cleanses" the surface in preparation of future applications of water-based cement.

FIG. 1 is a block diagram of a surface wettability test apparatus 100. The apparatus 100 comprises a TDR controller 102, which includes a signal generator 104 and a receiver 106. The signal generator 104 generates an "incident" electrical signal pulse that travels the length of a conductor/cable 114 and is reflected by the termination or "end" of the conductor/cable 114 (the "response" pulse). The incident pulse must be of short duration in order to not interfere with the response pulse. In one embodiment, the incident pulse has an amplitude of +5V, a rise time of 18 ns, an "active on" time of 18 ns, and a fall time of 18 ns, but other pulse values may be effective. In addition, in this embodiment, the conductor/cable 114 used commercially available RG58 50 ohm cable which resulted in a lag time between the incident and response pulse of approximately 200 ns. Both the generator 104 and receiver 106 are in electrical contact with first and second electrodes 108, 110 respectfully, via conductors/cables 114 of a known impedance. The electrodes are positioned along a surface 112 and are electrically insulated from each other. The apparatus 100 may represent several embodiments including, but not limited to, a laboratory tool or a sensor tool attached to the casing downhole.

As disclosed herein, the test apparatus 100, as employed as a laboratory tool, can be used to determine the length of time necessary to clean surfaces in anticipation of cementing operations and to test various compositions of surface-based fluids prior to employment of those fluids in a wellbore. As applied to a casing surface downhole, the apparatus 100 can monitor the surface wettability of the casing surface during several operations, including but not limited to drilling, cleaning, and cementing operations.

Figure 2A:
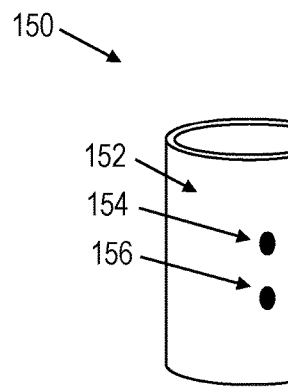
FIGS. 2A and 2B are schematic diagrams of electrodes mounted on surfaces.

FIG. 2A is an illustrative example of a surface wettability measurement configuration 150. A pair of first and second electrodes 154, 156 are mounted on the outside surface of a casing segment 152. In this embodiment, the electrodes 154, 156 are mounted flush with the outside surface of the casing 152 so as to not cause any disturbances of impediments to fluid flow on the outside of the casing. Additionally, the electrodes are electrically insulated from each other. Located such, the pair of electrodes will undergo shear force and are situated to measure surface wettability of the casing segment surface using TDR technology.

Figure 2B:
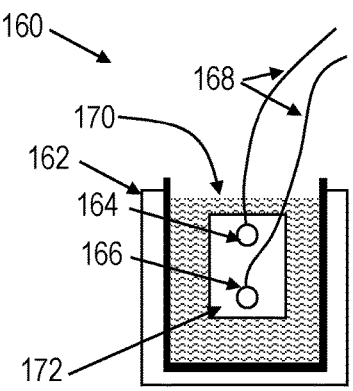

FIG. 2B is an illustrative example of a laboratory test setup for measuring surface wettability 160. A pair of first and second electrodes 164, 166 are mounted on a surface 172 which is immersed in a container 162 containing fluid 170. The electrodes are electrically connected to a pair of conductors/cables 168 which terminates at the TDR controller (not shown). Located such, when either the surface 172 is rotated or the container 162 is rotated, the pair of electrodes 162, 164 will undergo shear force similar to that experienced by fluid flow around a casing segment in a downhole environment. In this manner, conditions are sufficient to emulate downhole conditions to measure surface wettability of the casing segment surface using TDR technology.

Simulated downhole conditions of fluid flow around a casing, including shear, can be emulated in a lab environment by placing a cylindrical "bob" containing a pair of electrodes into a fluid and rotating the bob rapidly in relation to the fluid by using a motor or other device to rotate either the bob or the container holding the fluid. The rotating fluid emulates conditions experienced by the outside surface of the casing in a downhole environment. Alternatively, in another embodiment, the bob includes a single electrode and the container comprises the second electrode. For this alternative embodiment, a conductor/cable is attached to the electrode on the bob and another conductor/cable is attached to the container to measure the impedance of the surrounding fluid.

Figure 3A:
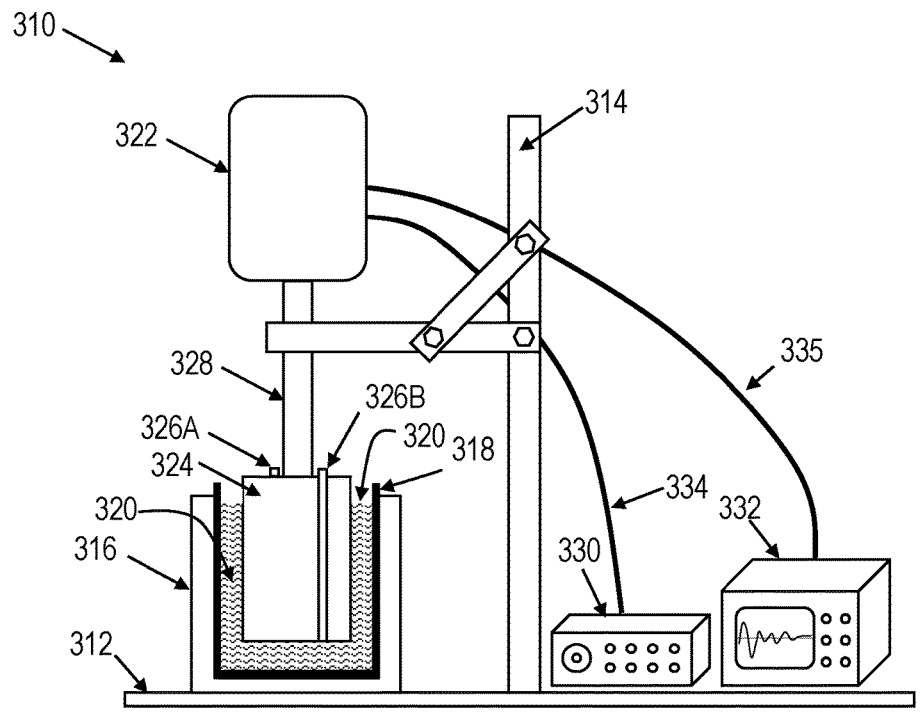
FIGS. 3A and 3B are schematic diagrams of a test apparatus to measure surface wettability of a surface utilizing time domain reflectometry techniques.

Accordingly, FIG. 3A is a schematic of a surface wettability test apparatus 310 for measuring the change in surface wetting on a metal surface, which can be used, for example, to simulate a metal surface including, but not limited to, a casing exterior surface in a well. The apparatus 310 is comprised of a test table 312, a test stand 314, a heater jacket 316, a container 318, a fluid under test 320, a motor 322, a bob assembly 324, a first electrode 326A, a second electrode 326B, a shaft 328, a signal source 330, a measurement device 332, an "incident" input cable 334, and a "response" output cable 335. This apparatus measures the change in surface wetting on an electrode surface from a first liquid phase to a second liquid phase as the electrodes undergo cleaning due to application of a shear force which is created by the relative motion between the electrode surface and the second liquid phase. The electrode surfaces can simulate the metallic body of a tubular. The first liquid phase can simulate a prior oil film formed on the surface. The second fluid can simulate the cleaning of an oil film by a water-based spacer fluid.

The test stand 314 is fixably attached to the test table 312 using any commercially available mechanical means. Both the stand 314 and table 312 can be made of wood, metal, plastic, or any other commercially-available structural materials. The heater jacket 316 is designed to hold the container 318 in place and aligned with the motor 322 and shaft 328 and is isolated electrically from the test stand 314. The container 318 may be constructed of a thermally conducting material and should have enough structural integrity so as to hold a fluid without leaking and to be able to resist deformation during tests where the bob 324 is spinning with a fluid 320 present. The test table 312 holds the heater jacket 316 in a set position using screws, adhesive, welds, clamps, or any commercially available means to maintain alignment between the heater jacket 316 and the motor 322. In an alternative embodiment, the motor 322 is configured to rotate the heater jacket 316 and imparts a rotation motion to the fluid 320 while the bob 324 remains stationary. The test table 312 and stand 314 may be constructed of any structural material including, but not limited to metal, plastic, or wood. The test stand 314 is designed to hold the motor 322 in vertical alignment with the heater jacket 316 so that the central axis of the motor 322 is in close alignment with the center of the heater jacket 316 as viewed from the top of the test apparatus 310. The bob 324 is a structural part that may be, but is not required to be cylindrical in shape. In the present embodiment, the test structure is illustrated by the bob 324 suspended from a motor 322; however, any other geometry capable of creating a measurable, repeatable shear application on the electrodes can be used. The bob 324 is fixably attached to the shaft 328, which is a structural device similar to a pipe and fixably mounts the bob 324 to the motor 322 to allow rotation of the bob 324 when the motor 322 turns. The motor 322 provides rotational speed to the bob assembly and may be, but is not limited to, an electrical motor or a mechanical device. In this embodiment, the motor 322 is an electrically-powered motor which can be either a conventional motor or stepper motor which is operably connected to rotate the bob 324 and move the surfaces in the test fluid 320. The bob 324 may contain passages (not shown) to allow conductors/cables 334, 335 which are operatively connected to the electrodes 326A, 326B to pass through the shaft 328. The bob 324 is constructed of an insulating material such as plastic or wood and holds the first and second electrodes 326A, 326B in fixed alignment with each other. In another embodiment, the shaft 328 is made of conductive material and acts as one conductor, the other conductor being the inner surface of the container 318 holding the second fluid. In a further embodiment, concentric telescoped insulated shafts are provided as conductors for the electrodes.

The electrodes 326A, 326B may be attached to the bob 324 employing a friction fit, adhesive, or other commercially available techniques so as to prevent movement of the electrodes 326A, 326B during rotation of the bob 324. The conductors/cables 334, 335 are operatively connected to the signal source such as a signal generator and a measurement device 332 such as an oscilloscope. Each of the first and second electrodes 326A, 326B comprise sections mounted on the bob 324. The electrodes are electrically insulated from each other. The bob 324 separates and isolates the first electrode 326A from the second electrode 326B. If the shaft 328 is comprised of conductive materials such as a metal, the electrodes 326A, 326B are mounted such that they are electrically insulated from the shaft 328.

The apparatus 310 is adapted for simulating and measuring the downhole wettability conditions and/or removal of any wetting or coating or film on the surfaces the electrodes 326A, 326B in the presence of a first test fluid 320. The changes can be measured under shearing conditions applied to the first test fluid 320 in the apparatus 310 which represent (to some extent) the conditions present in a well. The composition of the test fluid 320 can be kept constant during a testing procedure or it can be changed continuously or intermittently by dosing another test fluid that displaces the original fluid under controlled hydrodynamic conditions. In general, the apparatus 310 and applied voltage is adapted such that the electrical circuit is directed across the electrodes 326A, 326B through the test fluid. In general, the apparatus 310 can be used, as described herein, to measure any changes in any surface wetting or film on the test electrodes under such simulated test conditions and with such test fluids.

TDR measurements require accurate knowledge of the length of conductors or cables used. In both lab and downhole environments, this is deduced by either measuring the lengths of the conductors/cables or using known lengths of conductors/cables. Another variable of interest is the velocity factor, or speed of the signals in the measurement system relative to the speed of light, which is calculated by this equation:

$$V = \frac{1}{c}\left[\frac{l_c + l_m}{t_c + t_m}\right] \quad \text{[Equation 1]}$$

where V is the velocity factor, c is the speed of light, $l_c$ is the length of the conductor/cable (known), $l_m$ is the length of the probe which passes through the fluid (measured), $t_c$ is the speed of light through the conductor/cable, and $t_m$ is the speed of light through the medium (fluid). Thus measured, the total dielectric constant of the system under test can be determined.

In an example scenario, the electrodes are initially cleaned of all fluid and then are dipped in spacer fluid. Since spacer fluid is water-based, the electrodes will be short circuited. This is verified by sending a positive electrical pulse to the electrodes and measuring the reflected response pulse (which in the case of a short circuit is negative). Next, the electrodes are coated with an oil-based mud. Since an oil film is now deposited on the electrodes, it acts as an insulator for electrical signals and thus creates an open circuit condition between the electrodes. A TDR test will now show a reflected response pulse which is positive which indicates an open circuit termination as expected.

Figure 3B:
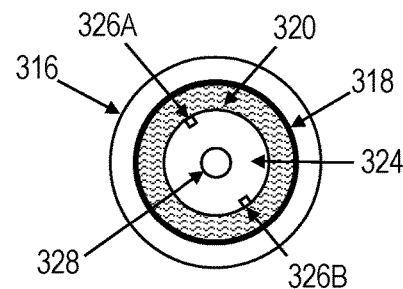

FIG. 3B shows the top view of the bob assembly 324 and heater jacket 316 in alignment with the container 318, illustrating the insulated separation of the electrodes in the container 318 of the apparatus 310. The bob 324 includes first and second electrodes 326A, 326B. The container 318 contains a test fluid 320 in which a bob 324 is inserted. In this embodiment, the electrodes 326A, 326B are flush with the outer surface of the bob 324 but other embodiments are possible including subletting the electrodes below the surface of the bob 324 or extending the electrodes so that they extend outward from the surface of the bob 324. Rotation of the bob 324 by the motor 322 (not shown) will generate a shear force in the fluid across the surface of the bob 324 and thus simulate fluid flow in a downhole condition. TDR readings may take place during this time to measure the length of time to clean the surface of the bob 324 under various mixtures of oil- and water-based fluids.

The primary method of cleaning of oil-wet surfaces in the wellbore is through chemical and mechanical action through application of wall shear applied at the surface due to flow of the spacer fluid. In order to mimic the pumping process in the wellbore, a motor is used in a laboratory test apparatus to apply a wall-shear rate through rotation of the bob 324 in relation to the fluid 320. The rotation of the bob 324 immersed in the fluid 320 generates the shear in the fluid and thus simulates cleaning. The composition of the test fluid 320 can be kept constant during a testing procedure or it can be changed continuously or intermittently by introducing another sample fluid that displaces the original fluid under controlled hydrodynamic conditions. In general, the system and applied voltage is adapted such that the electrical circuit is directed across the electrodes 326A, 326B through the test fluid 320.

One or both the electrodes 326A, 326B can be used to simulate a downhole metallic or formation material, such as an environment containing a steel tubular and formation rock. The test conditions of shear can be adapted to represent downhole conditions and the test fluid may correspond to fluids used in a wellbore. In general, the system 310 (FIG. 3A) can be used, as described herein, to measure any changes in any surface wetting on the test electrodes under such simulated test conditions and with such test fluids. The apparatus 310 (FIG. 3A) can be used to determine the removal of a film or coating on a metallic electrode surface that is needed to be removed under the effect of shear and time conditions as may be felt in the wellbore. Here, the coating can be deliberately created by applying a coating manually, for example, by dipping the electrodes in the coating fluid or can be emulated by the process of spinning the bob/electrode carrying assembly in the coating fluid, thereby causing shearing action by the fluid. In this embodiment, the contents and ingredients of the coating will be present in the first fluid. The second fluid will be used to partially or completely remove the coating. Alternately, the container can also be spun while keeping the bob static.

Figure 4A:
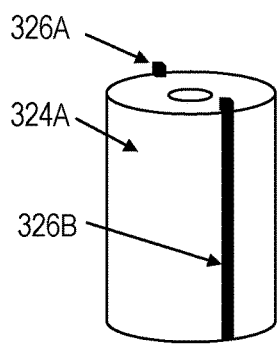
FIGS. 4A, 4B, and 4C are schematic diagrams of various electrode configurations.
Figure 4B:
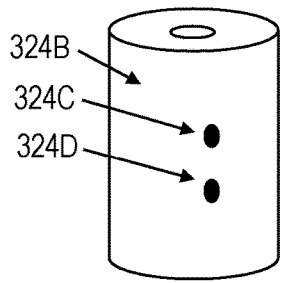
Figure 4C:
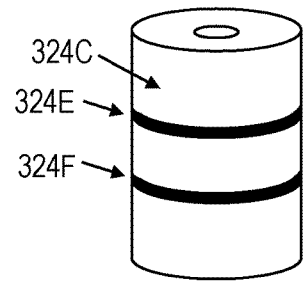

The bob 324 and arrangement of the electrodes 326A, 326B may take several forms as seen in FIGS. 4A, 4B, and 4C. FIG. 4A is a bob 324A and first and second electrodes 326A, 326B. In this configuration, the electrodes are composed of long linear bars of conducting material including, but not limited to metal. Embedded within the exterior surface of the bob 324A are at least two electrodes 326A, 326B.

The bob 324A is constructed of non-conducting material such as carbon fiber, wood, phenolic, or plastic including nylon. The bob 324 may employ a bearing assembly or other embodiments to allow electrical connections to be maintained while a bob and shaft assembly is rotated during test. The electrodes are electrically connected to a signal generator through the shaft by employment of wires, electrical contacts, electrical contact wipes, and/or a slip ring apparatus to allow the bob to rotate and still maintain an electrical connection to the test apparatus. The electrodes should preferably be mounted flush with the exterior of the bob to avoid physical damage during use and also to avoid unwanted agitation of the fluid under test which may affect sensor readings.

FIG. 4B shows an alternative electrode arrangement where at least two electrodes 324C, 324D are comprised of point contacts and may be, but are not required to be mounted flush with the exterior surface of the bob 324B.

FIG. 4C shows another alternative electrode arrangement where the at least two electrodes 324E, 324F are comprised of coaxial rings around the outer surface of the bob 324C. In these and other embodiments, local conditions and characteristics of fluid flow in a particular wellbore and/or test may help determine to optimum configuration of electrodes as they are mounted in the bob. Other embodiments are possible and are not limited herein.

Figure 5:
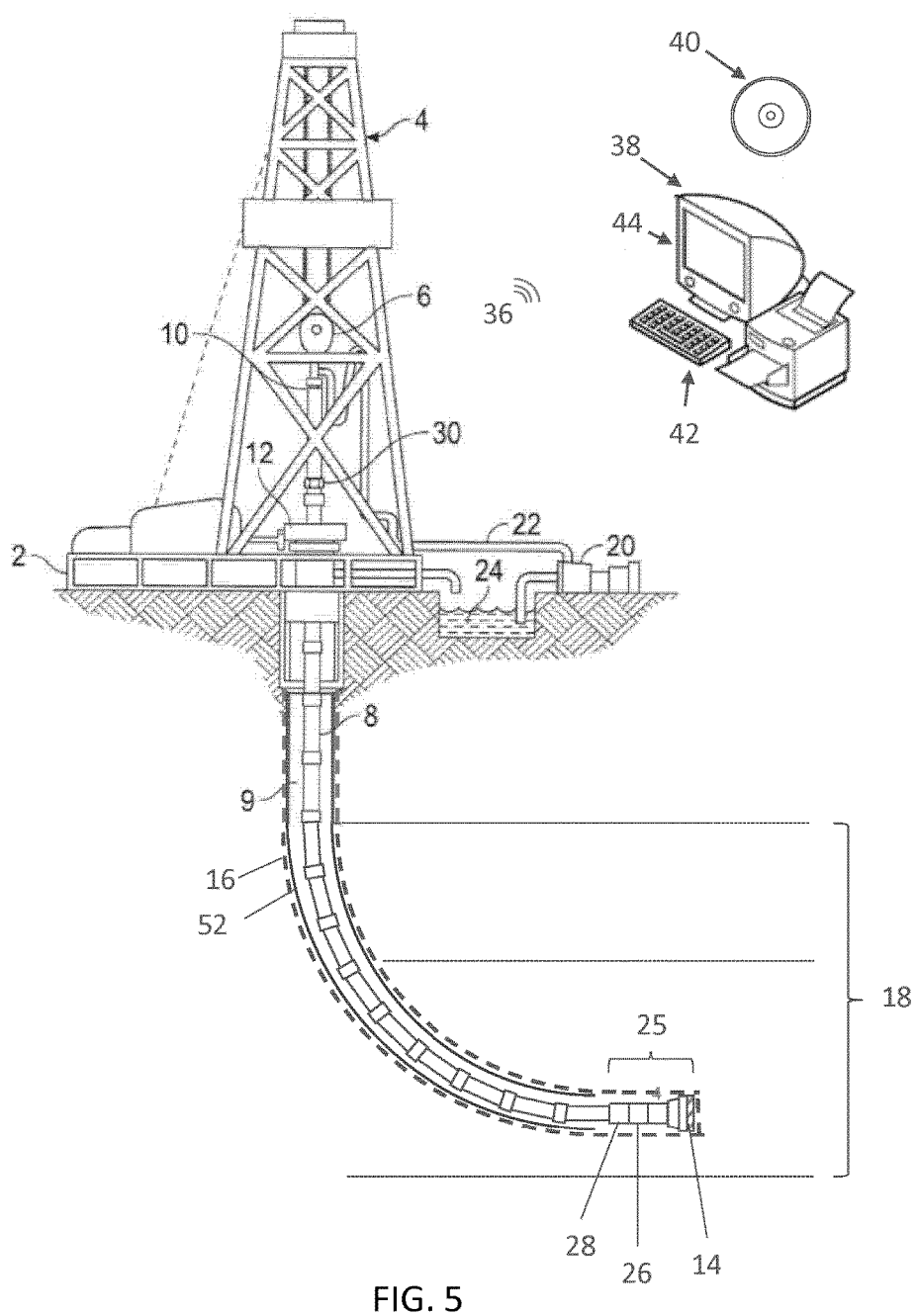
FIG. 5 is a schematic diagram of an illustrative downhole environment.

FIG. 5 shows an illustrative drilling environment in which surface wettability may be measured using TDR as described herein. A drilling platform 2 supports a derrick 4 having a traveling block 6 for raising and lowering a drill string 8. A drill string kelly 10 supports the rest of the drill string 8 as it is lowered through a rotary table 12. The rotary table 12 rotates the drill string 8, thereby turning a drill bit 14. Additionally or alternatively, rotation of the drill bit 14 is controlled using a mud motor or other rotation mechanism. As the drill bit 14 rotates, it creates a borehole 16 (represented using dashed lines) that passes through various formations 18. A pump 20 circulates drilling fluid through a feed pipe 22 to the kelly 10, downhole through the interior of drill string 8, through orifices in the drill bit 14, back to the surface via the annulus 9 around the drill string 8, and into a retention pit 24. The drilling fluid transports cuttings from the borehole 16 into the retention pit 24 and aids in maintaining the integrity of the borehole 16.

The drill bit 14 is just one piece of a bottom-hole assembly 25 that includes one or more drill collars 26 and logging tool 28. Drill collars 26 are thick-walled steel pipe sections that provide weight and rigidity for the drilling process. The logging tool 28 (which may be built into one of the drill collars) gathers measurements of various drilling or formation parameters. Without limitation, logging tool 28 may be integrated into the bottom-hole assembly 25 near the bit 14 to collect measurements. The collected measurements may be plotted and used for steering the drill string 8, monitoring drilling performance, and/or to analyze formation properties. Measurements from the logging tool 28 can be acquired by a telemetry sub (e.g., integrated with logging tool 28) to be stored in internal memory and/or communicated to the surface via a communications link. Mud pulse telemetry is one common technique for providing a communications link for transferring logging measurements to a surface receiver 30 and for receiving commands from the surface, but other telemetry techniques can also be used.

The telemetry signals are supplied via a wired or wireless communications link 36 to a computer 38 or some other form of a data processing device. Computer 38 operates in accordance with software (which may be stored on information storage media 40) and user input via an input device 42 to process and decode the received signals. The resulting telemetry data may be further analyzed and processed by computer 38 to generate a display of useful information on a computer monitor 44 or some other form of a display device including a tablet computer. For example, an operator could employ this system to obtain and monitor drilling parameters or formation properties. The computer 38 or another computer may also enable a drilling operator to adjust drilling operations based on the predicted casing wear output from a data-driven model (or related data such as a warning).

In the drilling environment of FIG. 5, some well completion operations, including installation of a casing 52 representing at least one casing section, have been performed. Post-drilling installation of casing segments have been completed. Each casing section involves joining modular casing segments until a desired casing section length is reached and/or lowering the casing section to a desired position in borehole 16. Once a desired length and position for a particular casing section is achieved, cementing operations are performed, resulting in a permanent casing section installation. As needed, the borehole 16 is extended by drilling through cement at an installed casing section terminus. The process of installing casing sections and extending 16 borehole can be repeated as desired. During drilling and/or well completion operations, the drill string 8 is routinely removed from the borehole 16, optionally reconfigured, and put back into the borehole 16 to continue the drilling process.

Figure 6:
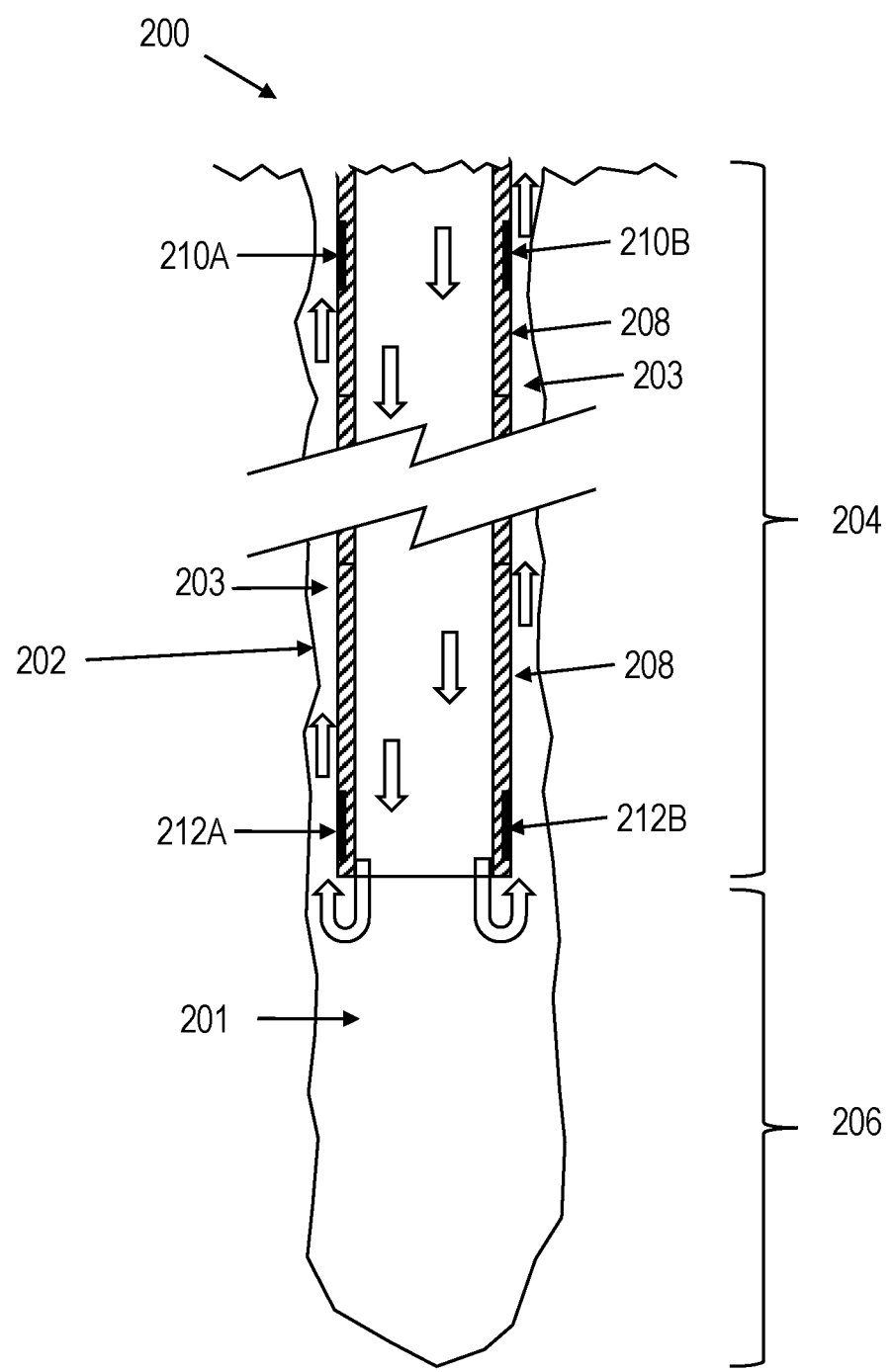
FIG. 6 is a schematic diagram of an illustrative downhole cleansing and time domain reflectometry technique.

FIG. 6 is an illustrative schematic diagram of an example cased borehole environment 200. The environment includes a borehole 201, a cased section 204, and an uncased section 206. The cased section 204 contains a casing string comprised of a plurality of individual casing segments 208. Each casing segment is fixably attached to the next casing segment by using threads or adapters (not shown). Prior to well operations, the space between the casing sections 208 and the wall of the borehole 202, known as the annulus 203, will be filled with cement to permanently attach the casing string to the borehole to prevent unwanted leaks of fluid and improve wellbore stability. At least one pair of electrodes 210A, 210B are located on at least one casing segment 208, configured as to allow the electrodes to be exposed to the annulus 203 and are in electrical isolation from each other and the casing segment 208. The electrodes 210A, 210B are electrically connected via a conductor/cable (not shown) to a TDR controller (not shown). In the preferred embodiment, the electrodes 210A, 201B are installed flush with the exterior surface of the casing segment 208 in order to closely experience actual surface flow conditions of the casing segment 208. In this manner, the electrodes 210A, 210B will experience the same surface based fluid concentrations the rest of the casing segment's 208 exterior surface will experience and give the most accurate readings for the TDR test equipment.

In the preferred embodiment, spacer fluid, used as a cleaner fluid to remove oil-based fluid, is pumped into the well and down through the casing string (which has not yet been cemented) and then out the lower end of the casing segment 208 and up through the annulus 203 between the outside of the casing 208 and the borehole 201. As the spacer fluid displaces the prior fluid in the borehole, there is intermingling and mixing between the prior fluid and the spacer fluid. The intermingled fluid includes varying mixtures of the prior fluid in the well and spacer fluid. Such a fluid is sometimes referred to as contaminated spacer fluid. The spacer fluid being pumped behind the intermingled fluid is sometimes referred to as pure or uncontaminated spacer fluid.

In another embodiment, more than one set of electrodes may be installed on the casing string. As seen in FIG. 6, a plurality of electrode pairs are present (210A, 210B and 212A, 212B shown) and are in electrical isolation from each other and the casing segment 208. Each pair of electrodes are electrically connected using conductors/cables (not shown) to a TDR controller (not shown) for signal injection, reception, and analysis by the operator. By using several pairs of electrodes, a surface operator may monitor the progress of cleansing of the borehole 201 in preparation for cementing operations.

Figure 7A:
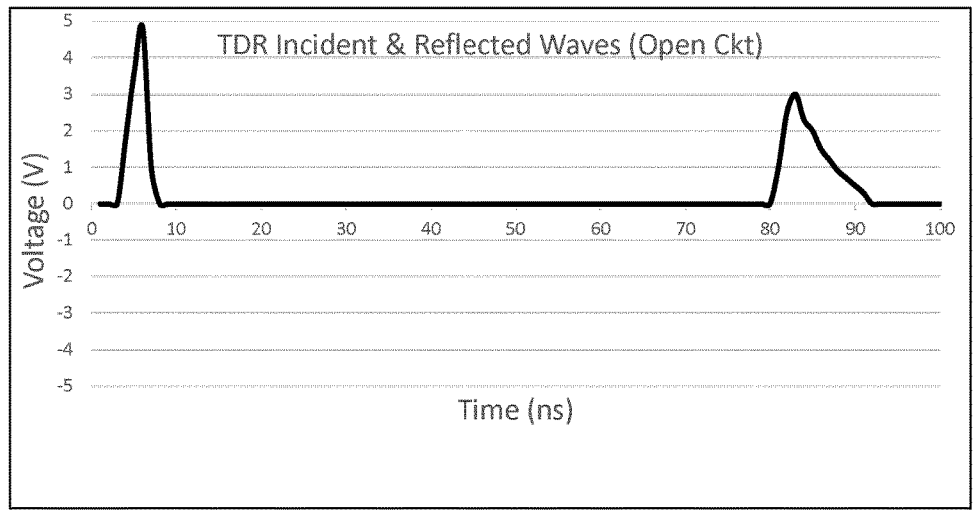
FIGS. 7A and 7B are graphs of illustrative time domain reflectometry measurements.
Figure 7B:
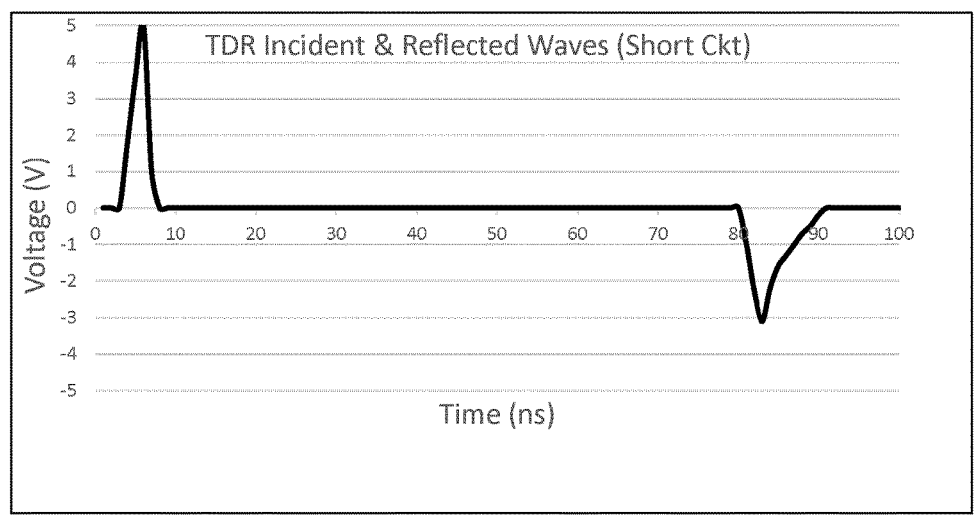

FIGS. 7A and 7B are graphs of "incident" input and "reflected" output waves in a TDR measurement system. Mathematically, the complex amplitude of the reflected pulse is related to the complex amplitude of the incident pulse by a factor known as the reflection coefficient ρ. The reflection coefficient ρ is in turn determined by the impedances of the transmission line (cable) and the termination.

$$\rho = \frac{A_{reflected}}{A_{incident}} \quad \text{[Equation 2]}$$

$$\rho = \frac{Z_{termination} - Z_{cable}}{Z_{termination} + Z_{cable}} \quad \text{[Equation 3]}$$

If the cable impedance remains constant, any changes in the termination impedance will show up in the measured amplitude of the reflected pulse. Thus, in scenarios where termination impedance undergoes a change (e.g. when an oil-wet electrode undergoes cleaning and becomes water-wet), this can be used to accurately measure the degree of the change of impedance (e.g. the degree of cleaning of the electrode) and thus the surface wettability of the region immediately near the electrodes. A continuous monitoring of the amplitude of reflected waves can thus be used to continuously monitor the cleaning of the electrodes and thus the presence of the proper environment for placing cement into the borehole.

The process of cleaning a casing section or a bob in a test stand involves sending an electrical signal to the electrodes and measuring the reflected signal. The incident pulse is a positive signal that is sent to the electrodes in physical contact with the fluid under test. The initial reflected pulse shows a positive return pulse as seen in FIG. 7A indicating the presence of an oil-based coating. Over time, as the water-based spacer fluid is circulated over the surface, the oil-based fluid is gradually removed and replaced with a water-based fluid. As the water-based fluid becomes more prevalent, the reflected wave received by the test equipment becomes negative as seen in FIG. 7B. In this way, continual monitoring of the downhole conditions can accurately alert the operator when the oil-based fluid is removed and conditions for cementing are in place.

Figure 8:
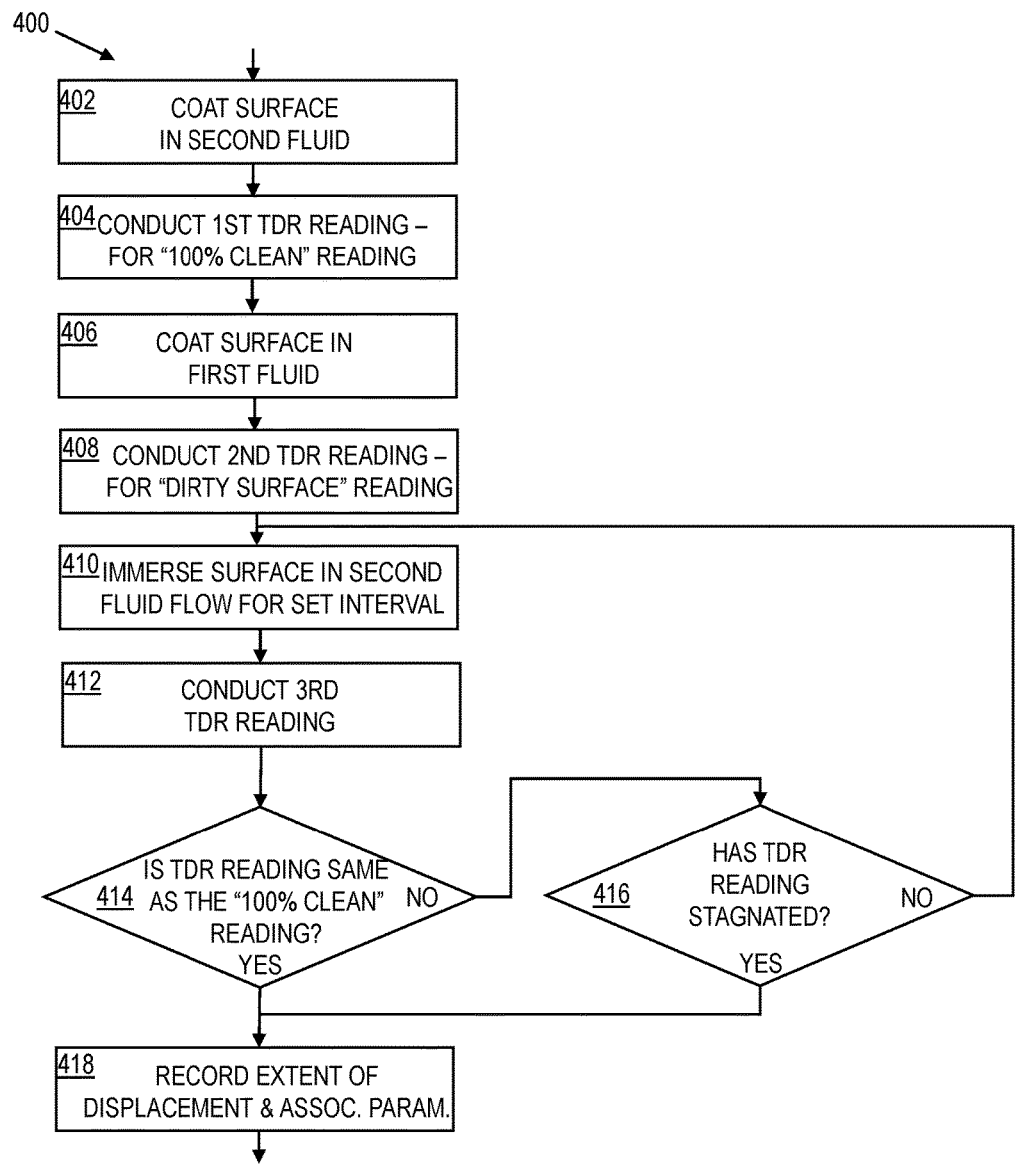
FIG. 8 is a flowchart showing a method for determining the surface wettability of a surface using time domain reflectometry techniques.

FIG. 8 is a block diagram 400 for a TDR sensor system to determine the surface wettability of a fluid on a surface. At block 402, the clean surface is dipped in the second water-based fluid to establish a "clean" response when measured using TDR technology. In well operations, this step might have to take place prior to deployment in a wellbore. In a lab environment, the surface may be dipped in spacer fluid. At block 404, conduct the first TDR reading for a "100% clean" reading to be used as a reference for further measurements. At block 406, dip the surface in a first fluid, an oil-based mud. In a well environment, this can occur as a consequence of drilling operations. In a lab environment, the surface should be coated with an oil-based mud. At block 408, conduct a second TDR reading of the surface to verify a "dirty surface" reading of a surface covered in oil-based fluid. At block 410, immerse the surface into a fluid flow comprised of the second, water-based fluid for a set interval of time. In a well environment, the fluid flow is created by the pump located on the surface circulating fluid while in a lab environment, fluid flow is emulated by using a rotating surface, a rotating container, or by at least one pump moving the second fluid across the surface. At block 412, conduct a third TDR reading to measure the extent of displacing the first fluid off of the surface under test. At block 414, a decision must be made: is the third TDR reading the same as the "100% clean" reading? If yes, this means that the surface is completely clean and the first fluid has been totally displaced by the second fluid. If, however, the third TDR measurement does not match the "100% clean" reading, a separate decision should be made. At block 416, a decision must be made: has the third TDR reading stagnated across several iterations? If no, continue the displacing process by continuing the fluid flow for a set interval and repeating the third TDR measurement. If the third TDR measurement has shown that no additional changes have occurred, that the maximum level of displacement of the first fluid has taken place and the process can stop. At block 418, record extent of displacement and associated parameters. Once the displacement steps have been completed, various parameters such as interval of time, characteristics of the second fluid, level of cleaning, etc. may be recorded for future reference.

Embodiments disclosed herein include:

A: a surface wettability measurement method comprising: providing first and second electrodes on a surface, said electrodes electrically insulated from each other; coating the surface with a first fluid; displacing the first fluid off of the surface using a second fluid; at least once during or after said displacing, sending an electrical pulse to the first and second electrodes and measuring the reflected pulse using time domain reflectometry (TDR) techniques; and determining, based on the reflected pulse, whether the surface has been wetted by the second fluid.

B: a surface wettability measurement system, comprising: a first and second electrode integrated with a surface, said electrodes electrically insulated from each other; a signal generator; and a time domain reflectometry (TDR) controller coupled to the first and second electrodes, wherein the TDR controller obtains a TDR measurement while or after a displacing fluid moves over a surface, wherein the TDR measurement indicates a surface wettability of the surface.

Each of embodiments A and B may have one or more of the following additional elements in any combination: Element 1: further comprising ceasing said displacing in response to determining that the surface has been wetted. Element 2: further comprising increasing the fluid flow rate of the second fluid in response to determining that the surface has not been wetted. Element 3: further comprising adjusting an attribute of the second fluid in response to determining that the surface has not been wetted. Element 4: further comprising selecting or updating a displacement time interval in response to determining that the surface has been wetted. Element 5: further comprising commencing cementing operations in response to determining that the surface has been wetted. Element 6: wherein the first fluid is oil-based. Element 7: wherein the second fluid is water-based. Element 8: wherein the surface is part of a surface wettability test apparatus located at the earth's surface. Element 9: wherein the surface is an exterior surface of a casing deployed downhole in a wellbore. Element 10: wherein the first and second electrodes are positioned along an outside surface of a casing in a downhole environment. Element 11: further comprising a plurality of electrode pairs positioned along an outside surface of a casing in a downhole environment to enable wettability measurements at multiple positions along the outside surface of the casing. Element 12: wherein the surface is a component of a surface wettability test apparatus located at earth's surface. Element 13: wherein the test apparatus further includes a rotating bob to cause the displacing fluid to flow across the surface. Element 14: wherein the test apparatus further includes a rotating container to cause the displacing fluid to flow across the surface. Element 15: wherein the test apparatus further includes at least one fluid pump to cause the displacing fluid to flow across the surface. Element 16: further comprising a cementing controller that initiates a cementing operation in response to the TDR measurement indicating that the surface has been wetted.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A surface wettability measurement method comprising:
   providing first and second electrodes on a surface, said electrodes electrically insulated from each other;
   coating the surface with a first fluid;
   displacing the first fluid off of the surface using a second fluid;
   at least once during or after said displacing, sending an electrical pulse to the first and second electrodes and measuring the reflected pulse using time domain reflectometry (TDR) techniques; and
   determining, based on the reflected pulse, whether the surface has been wetted by the second fluid.

2. The method of claim 1, further comprising ceasing said displacing in response to determining that the surface has been wetted.

3. The method of claim 1, further comprising increasing the fluid flow rate of the second fluid in response to determining that the surface has not been wetted.

4. The method of claim 1, further comprising adjusting an attribute of the second fluid in response to determining that the surface has not been wetted.

5. The method of claim 1, further comprising selecting or updating a displacement time interval in response to determining that the surface has been wetted.

6. The method according to any one of claims 1-5, further comprising commencing cementing operations in response to determining that the surface has been wetted.

7. The method of claim 1, wherein the first fluid is oil-based.

8. The method of claim 1, wherein the second fluid is water-based.

9. The method of claim 1, wherein the surface is part of a surface wettability test apparatus located at the earth's surface.

10. The method of claim 1, wherein the surface is an exterior surface of a casing deployed downhole in a wellbore.

11. A surface wettability measurement system, comprising:
    a first and second electrode integrated with a surface, said electrodes electrically insulated from each other;
    a signal generator; and
    a time domain reflectometry (TDR) controller coupled to the first and second electrodes, wherein the TDR controller obtains a TDR measurement while or after a displacing fluid moves over a surface, wherein the TDR measurement indicates a surface wettability of the surface.

12. The system of claim 11, wherein the first and second electrodes are positioned along an outside surface of a casing in a downhole environment.

13. The system of claim 11, further comprising a plurality of electrode pairs positioned along an outside surface of a casing in a downhole environment to enable wettability measurements at multiple positions along the outside surface of the casing.

14. The system of claim 11, wherein the surface is a component of a surface wettability test apparatus located at earth's surface.

15. The system of claim 14, wherein the test apparatus further includes a rotating bob to cause the displacing fluid to flow across the surface.

16. The system of claim 14, wherein the test apparatus further includes a rotating container to cause the displacing fluid to flow across the surface.

17. The system of claim 14, wherein the test apparatus further includes at least one fluid pump to cause the displacing fluid to flow across the surface.

18. The system of claim 14, further comprising a cementing controller that initiates a cementing operation in response to the TDR measurement indicating that the surface has been wetted.

* * * * *